United States Patent [19]

Fox et al.

[11] Patent Number: 4,648,542
[45] Date of Patent: Mar. 10, 1987

[54] DISPOSABLE STAPLER

[75] Inventors: William D. Fox; William M. Mereness, both of Cincinnati, Ohio

[73] Assignee: Senmed, Inc., Cincinnati, Ohio

[21] Appl. No.: 793,955

[22] Filed: Nov. 1, 1985

[51] Int. Cl.⁴ ............................................. A61B 17/00
[52] U.S. Cl. .................................... 227/19; 227/136; 227/DIG. 1; 227/121
[58] Field of Search ........... 227/19, 120, 136, DIG. 1, 227/121

[56] References Cited

U.S. PATENT DOCUMENTS

| | | |
|---|---|---|
| 1,910,688 | 4/1933 | Goodstein . |
| 1,945,377 | 1/1934 | Posnack . |
| 3,275,211 | 9/1966 | Hirsch et al. . |
| 3,583,622 | 6/1971 | Graeff ............................... 227/120 |
| 3,827,277 | 8/1974 | Weston ......................... 227/DIG. 1 |
| 3,873,016 | 3/1975 | Fishbein . |
| 3,906,957 | 9/1975 | Weston ......................... 227/DIG. 1 |
| 4,014,492 | 3/1977 | Rothfuss . |
| 4,127,227 | 11/1978 | Green . |
| 4,185,762 | 1/1980 | Froehlich . |
| 4,202,480 | 5/1980 | Annett . |
| 4,256,251 | 3/1981 | Moshofsky . |
| 4,321,002 | 3/1982 | Froelich . |
| 4,399,810 | 8/1983 | Samuels et al. . |
| 4,477,007 | 10/1984 | Foslien . |
| 4,477,008 | 10/1984 | Struble . |
| 4,505,273 | 3/1985 | Braun et al. . |
| 4,523,707 | 6/1985 | Blake, III et al. . |

FOREIGN PATENT DOCUMENTS

618955 7/1930 Fed. Rep. of Germany .
WO84/01706 5/1984 PCT Int'l Appl. .

Primary Examiner—Paul A. Bell
Attorney, Agent, or Firm—Wood, Herron & Evans

[57] ABSTRACT

A stapler having a pistol grip which can be entirely formed as a one-piece molding, without need for separate springs, connectors or other parts. The main springs are not stressed until the trigger is pulled for the first time. Staples of a special configuration are closed by a driver having a specially shaped forming end.

54 Claims, 18 Drawing Figures

DISPOSABLE STAPLER

FIELD OF THE INVENTION

This invention relates to staplers, and in an important aspect to a low cost stapler which can be made as and assembled from a unitary one-piece molding. The stapler is useful, among other applications, for suturing incisions and wounds in the skin.

BRIEF DESCRIPTION OF THE INVENTION

The stapler to which this invention is directed is of a fundamentally new configuration. This configuration enables it to be made as a unitary molding, although the stapler can also be assembled from separately molded parts. Because it can be made as a single molded part, this stapler can be produced less expensively than one assembled from many separate parts.

The present stapler is of the general type wherein the staple is closed "blind" from the top, on an anvil which projects into the staple itself, as distinguished from those wherein the staple is closed on an anvil which engages the staple from the back. Staplers of this general type are useful for suturing skin, closing packages, and other blind stapling situations where an anvil cannot be placed behind the object to be stapled.

The relatively low cost of this new stapler particularly adapts it for medical use; it is sufficiently inexpensive that it can be discarded after only a single use, rather than being sterilized for reuse.

While one-piece staplers are known, as shown in Struble U.S. Pat. No. 4,477,008, they have been operated by squeezing the fingers together transversely to the stapler axis. No previously known one-piece stapler has had a pistol grip by which it can be held in the palm and operated by squeezing a trigger in line with the axis of the stapler. Moreover, no known one-piece stapler has enabled the operator to apply a high degree of leverage in closing the staple. On the contrary, a relatively large force has previously been required to be applied between the finger tips, to form the staple; this made it difficult to use as light a force as is desirable in suturing a wound. The stapler of this invention provides a construction having a palm held hand grip and a lever trigger which provides good leverage to operate a staple former or driver to close the staple, and enables the operator to apply a soft touch in stapling. This feature is especially important for medical use.

The stapler is preferably formed as a single molding which includes a body section at one end, a trigger section at the opposite end, and a handle section between them. The handle section of the molding is folded or bent over itself to permit the trigger end section to be brought forwardly and down over the front end of the body section. The trigger section has an aperture which is sufficiently wide that the body section can be inserted into and partly through this aperture so that the trigger extends approximately perpendicularly to the body section. The driver extends from the trigger section and is inserted into a passage in the body as the trigger is being thus positioned. The folded-over handle portions lock together to form a pistol grip for the stapler.

In the preferred embodiment of the stapler of this invention, whether assembled from a one-piece molding or from separate parts, the drive is movable in a channel in the body to engage a staple and press it forwardly in a stapler guide passage against an anvil which depends from the front end of the body. Staples are fed between the driver and the anvil, into the guide passage. The trigger is pivotally mounted and is operated by pulling it rearwardly, toward the pistol grip. The trigger includes a finger-engaging portion below its pivot and a top part above the pivot; as the finger engaging portion is pulled back toward the grip, the top part swings forward. The top part of the trigger is connected rearwardly to the driver, at a position behind the trigger, by one or more straps, to pull the driver forwardly as the trigger is pulled back.

Staples are preferably supplied to the staple guide passage from a stack or magazine which feeds them sequentially into the passage on a right angular path from below. The staples are biased toward the guide passage by a feed spring. The open tips of the staple being applied are fully viewable by the operator; this results in part from the fact that the stapler is gripped below and rearwardly of the body, away from the staple applying tip.

When the trigger is operated to bring the driver into engagement with the first staple from the supply, a supplementary or backup spring is moved forward with the driver and is brought into engagement with the feed spring to increase the force exerted by the feed spring. An increasing force is thereby applied to urge the staple into the guide passage as the driver moves forward; this force decreases as the driver retracts. The backup spring is preferably formed as a part of the driver and extends beneath it into position to engage the feed spring. The backup spring is not stressed during shipment or storage, or until the trigger is first pulled; this avoids the creep or cold flow which has previously hampered use of plastic springs.

The stapler is preferably used with staples which in the open configuration are "M" or spider-shaped and which, in closed position, form what can be called a pentagonal "B" shape wherein the legs are inbent toward the center. This "B" shape is especially advantageous because it better resists rotation of the staple in the wound, so that those portions of the staple which were outside the skin at closure, remain outside thereafter. The "B" shape is also desirable because the large curves of the legs facilitate removal without tearing the skin. The staples are closed by straightening a rounded or U-shaped center section, without bending other parts of the staple. In such closure the stapler acts in a unique "soft touch" manner, by first exerting staple-closing force over a long lever arm to just the outer bends of the staple, to start to straighten the center bend, and then shortening the lever arm by moving the point of engagement by the driver closer to the center of the staple, as the outer portions of the staple legs become less accessible to the driver. In this manner the staples are closed smoothly without excessive hand force being required. In this procedure the staple cooperates with a specially configured staple-engaging end surface of the driver. Outer centering pockets of the driver first engage the staple outwardly adjacent the legs thereof; then inner pockets of the driver engage the staples closer to the center portion; this shortens the lever arm (the distance from the centerline of the staple to the point of engagement by the driver).

The formed staple is ejected from the anvil, when the driver is retracted, by an integral staple ejection spring which bears on the staple at the anvil and presses it off the anvil.

After the staple has been formed, the driver is retracted from its forwardmost position by a retract spring which preferably is formed as an S-shaped leaf spring between the pistol grip and the driver. A ratchet is provided to prevent the driver from being retracted from a staple once the driver has started pushing that staple toward the anvil. This mechanism prevents interposing a second staple into the path of the driver before an earlier staple has been ejected. As with the backup spring, the ratchet spring is not stressed until the stapler is used for the first time.

The stapler is supplied to the user in a configuration such that it is virtually ready for use but wherein the most important springs, that is, the backup spring, the driver retract spring, and the rathcet spring, are not loaded (stressed). They are loaded automatically as the trigger is first pulled. At the time of first use, the stapler is cocked by pulling the trigger to a point which brings the ratchet pawl past an initial stop, thereby loading it and preventing the trigger from returning to an uncocked position thereafter. At this point the backup spring is brought into engagement with the feed spring, and the driver is in position to engage a first staple. The unstressed condition of the springs prior to time of use provides an extended shelf life for the stapler.

DESCRIPTION OF THE DRAWINGS

The invention can best be further described and explained by reference to the accompanying drawings in which.

DETAILED DESCRIPTION

The stapler of this invention can be, and preferably is, formed as a unitary molding which incorporates, in one piece, a body, a pistol grip, a pivotable trigger, a staple driver or former, driver advance and return means, a staple holder or magazine, a staple feed spring, a backup feed spring, a driver advance ratchet, and a staple ejection spring. The drawings show the stapler as formed by a single piece molding, however, it should be understood that it can alternatively be assembled from two or more separately formed pieces. The stapler can be molded of a thermoplastic polyetherimide resin such as "Ultem 1000" or, as another example, from a polycarbonate resin such as "Lexan 124", both sold by General Electric Company. The molding process can be carried out by injection molding or other equivalent means.

A preferred form of unitary molding for this purpose is designated by 10, and is shown in FIGS. 1-4 in its unassembled state. The molding basically comprises three sections: a body section 11, a handle section 12, and a trigger section 13. The handle section lies between and connects the body and trigger sections. As described subsequently in greater detail, body section 11 preferably includes components forming a staple guide passage 15 (see FIGS. 10 and 12), a magazine or holder 16 from which staples are fed into the staple guide passage, a feed spring 17, an anvil 18, a staple ejection spring 19, a driver guide channel 20, the pawl 21 of a driver ratchet, and two laterally spaced trigger pivot openings 22. The middle or handle section 12 includes the forward part 26 of a pistol grip, an intermediate flexible or bendable portion 27 which forms the butt of the grip, the rear part 28 of the grip, and latch means 29, 29a for securing the front and rear grip components together. The trigger section 13 of molding 10 includes components forming a trigger 33, two stub pivot axles 34, a driver 35, a driver retract spring 36, the rack 37 of the driver ratchet, a backup or supplementary feed spring 38, and connecting means 40 between the trigger and the driver for pulling driver 35 forward when trigger 33 is pulled.

Figures 2, 3:
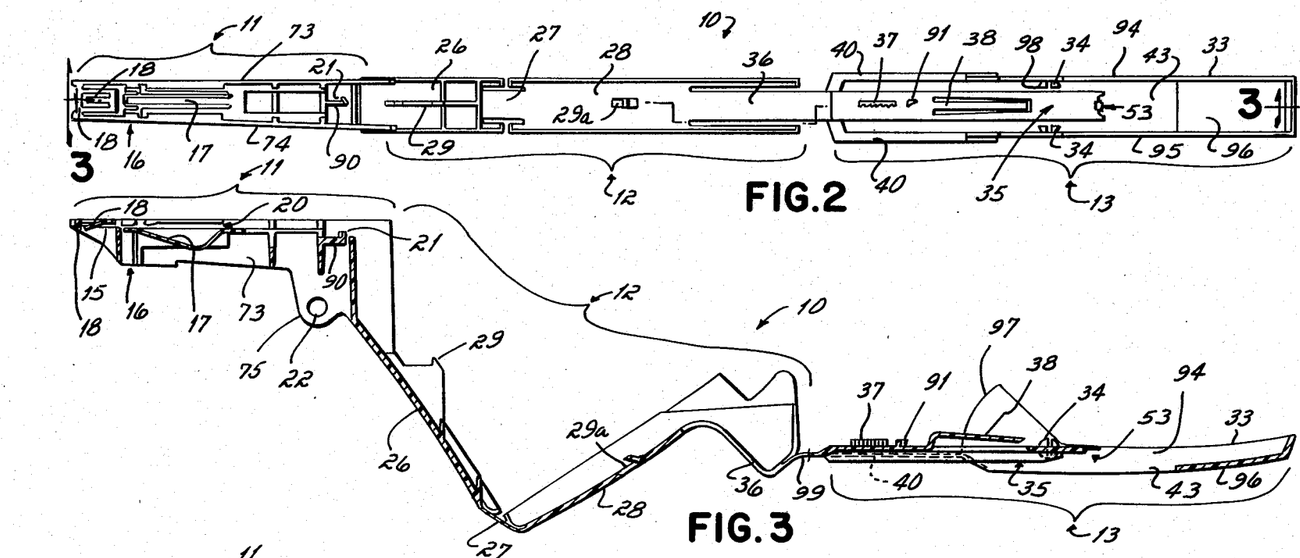
FIG. 2 is a top plan view of the one-piece molding shown in FIG. 1.
FIG. 3 is a longitudinal vertical section of the unassembled molded piece, taken on line 3—3 of FIG. 2.
Figure 4:
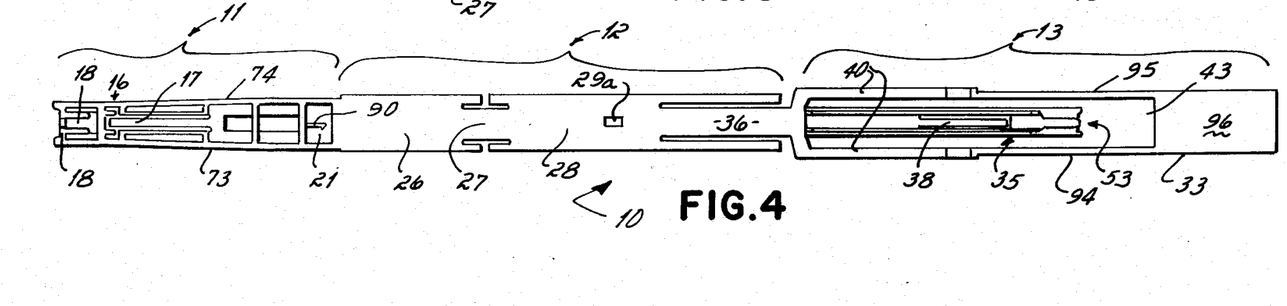
FIG. 4 is a plan view of the underside of the molded piece, prior to assembly.

To assemble the one-piece molding into the stapler, trigger section 13 is swung up and forward from the handle section so that it is above or overlying the body. Driver 35 is inserted into the driver guide channel 20 in the body so that it can slide forward therein. The trigger is pulled forward and over the front end of body section 11, which is passed partway through a body aperture 43 in the trigger section (FIG. 2). The trigger section is oriented so that trigger 33 extends at an angle, preferably substantially perpendicularly, to the body. The trigger sides can be flexed out so that pivot axles 34, 34 can be snapped into pivot openings 22, 22 in the body. The rear part 28 of the grip is latched to the front part 26 by hooking grip latch portion 29 into the cooperating opening 29a (see FIG. 5). The handle section 12 thereby forms a pistol grip type handle, rearwardly of the body and trigger, so that the trigger can be drawn to the grip to actuate the closure of a staple at the front end of the body sectin. This type of grip is more effective, from ergonometric considerations, than toggle-action means of the prior art which are operated between the fingertips.

Figures 5, 6:
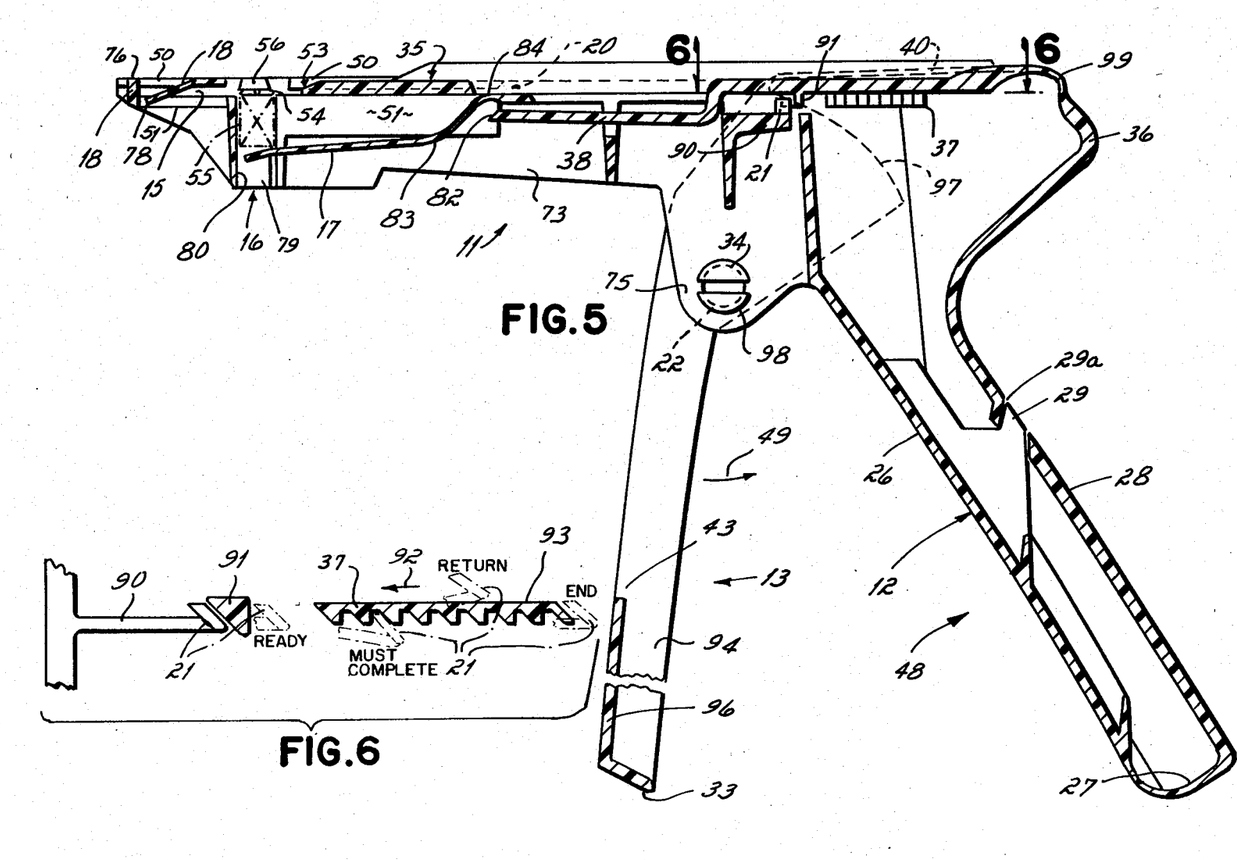
FIG. 5 is a vertical section of the assembled stapler in the "as-shipped" configuration, before the trigger has been pulled to advance the ratchet.
FIG. 6 is a fragmentary enlarged horizontal section taken on line 6—6 of FIG. 5, partly diagrammatic in nature, showing the relative positions of the pawl with respect to the stop and the ratchet at various stages of the operating cycle.

The various components of the stapler can best be further understood by reference to FIGS. 5 and following, which show the stapler in its assembled or use configuration. In the assembled stapler the trigger 33 is pivoted for counterclockwise movement toward grip 48 in the direction indicated by arrow 49, (FIG. 5). The trigger is connected rearwardly to driver 35, at a point behind the trigger, by connecting means comprising straps 40, 40 on each side of the driver (best seen in FIG. 2). Driver 35 slides in body 11 between upper and lower driver guide ways 50, 51 in body 11. The forward or tip end 53 of the driver (see FIGS. 14A–C) engages and pushes forward the uppermost staple 54 of a stack 55 of staples. Stack 55 is loaded into magazine 16 at the time the stapler is being assembled; or a separate magazine can be used. A visual counter or indicator can optionally be provided to show the number of staples remaining. The stack 55 of staples is urged upwardly in body 11 by feed spring 17, against an overhead bridge or staple retainer 56, in position to be engaged by the driver. Spring 17 is assisted by backup spring 38 which increases the upward force on the stack 55 of staples during closure of the staple. The top staple 54, when engaged by the driver, is moved forwadly from stack 55 and along staple guide passage 15 until it abuts the downwardly projecting anvil 18.

Figures 1, 15, 16:
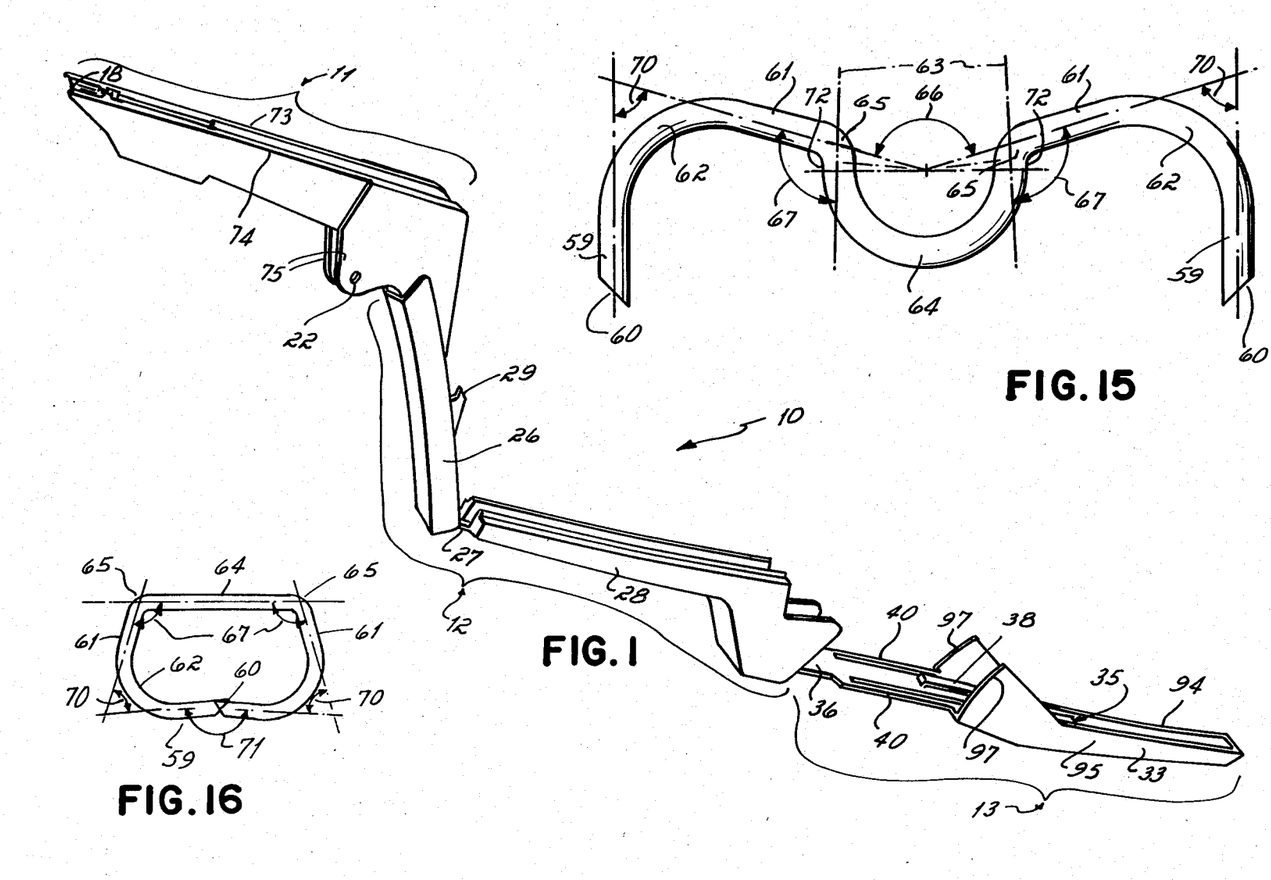
FIG. 1 is a perspective view of a preferred form of one-piece molding prior to assembly into a stapler according to the invention.
FIG. 15 is an enlarged plan view of a preferred form of staple in accordance with the invention, in the open condition.
FIG. 16 is a plan view of the staple in closed condition.
Figure 14A:
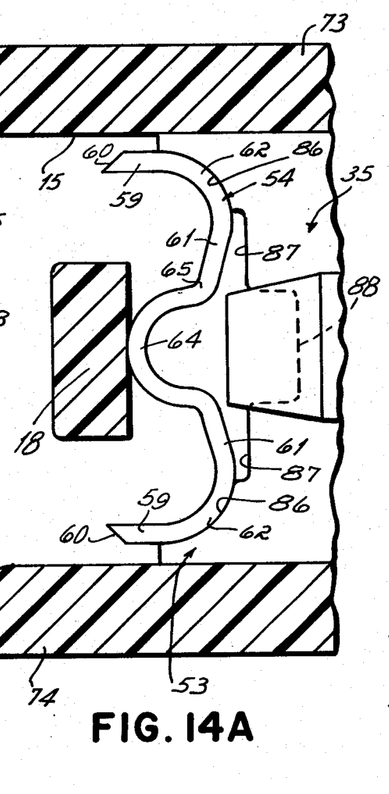
FIGS. 14A, B and C are a progressive series of enlarged horizontal sectional views of the front end of the stapler, showing a staple, driver, and anvil, as the staple is being formed, FIG. 14A showing the staple in open configuration when it is first engaged by the driver, FIG. 14B showing the staple after it has been partially formed on the anvil, and FIG. 14C showing the staple in fully formed or closed configuration.

A preferred form of staple 54 is shown enlarged in FIGS. 14A and 15 in its open or as-supplied configuration. The shape of the staple, prior to forming, is referred to herein as an "M" or "spider" shape. The staple has a pair of parallel, straight outer legs 59, 59 having pointed or chisel tips 60, 60. The legs 59, 59 are joined to straight intermediate sections 61, 61 by outer bends or knees 62, 62. The intermediate sections 61, 61 extend upwardly and outwardly from a rounded, preferably semicircular, center section 64 at inner bends 65, 65 to form an obtuse center angle 66 between them. The obtuse angle 66 between intermediate sections 61, 61 should preferably be about 140°–150°, most preferably 150°. The center section 64 is an arc, preferably of about 180°–188°, most preferably 184°, and is preferably extended by short straight sections 72,72, at its upper ends, just inwardly of inner bends 65, 65 so that the center section is preferably somewhat U-shaped. The intermediate section 61, 61 should form angles 67, 67 of about 100°–110°, most preferably 105°, with the axes 63 of the extensions 72,72 of the center section (see FIG. 15). The outer bends preferably form acute angles 70, 70 of about 70°–75°, most preferably 75°, between the intermediate sections 61, 61 and the legs, so that the outer legs are parallel to each other. Whatever the precise magnitude of the angles 67 and 70 of the inner and outer bends, collectively they should be such that when the center section 64 is straightened in closure, the legs will be slightlty inbent (about 2°–5°), as shown in FIG. 16. For this reason, the sum of the angles of an inner bend 65 and an outer bend 62 should be less than 180°, preferably about 178°. The staples may be made of about 0.02" diameter round stainless steel wire; they are usually quite small, and may, for example, be about 0.2" high by 0.4" wide in open form.

Figures 11, 12, 13:
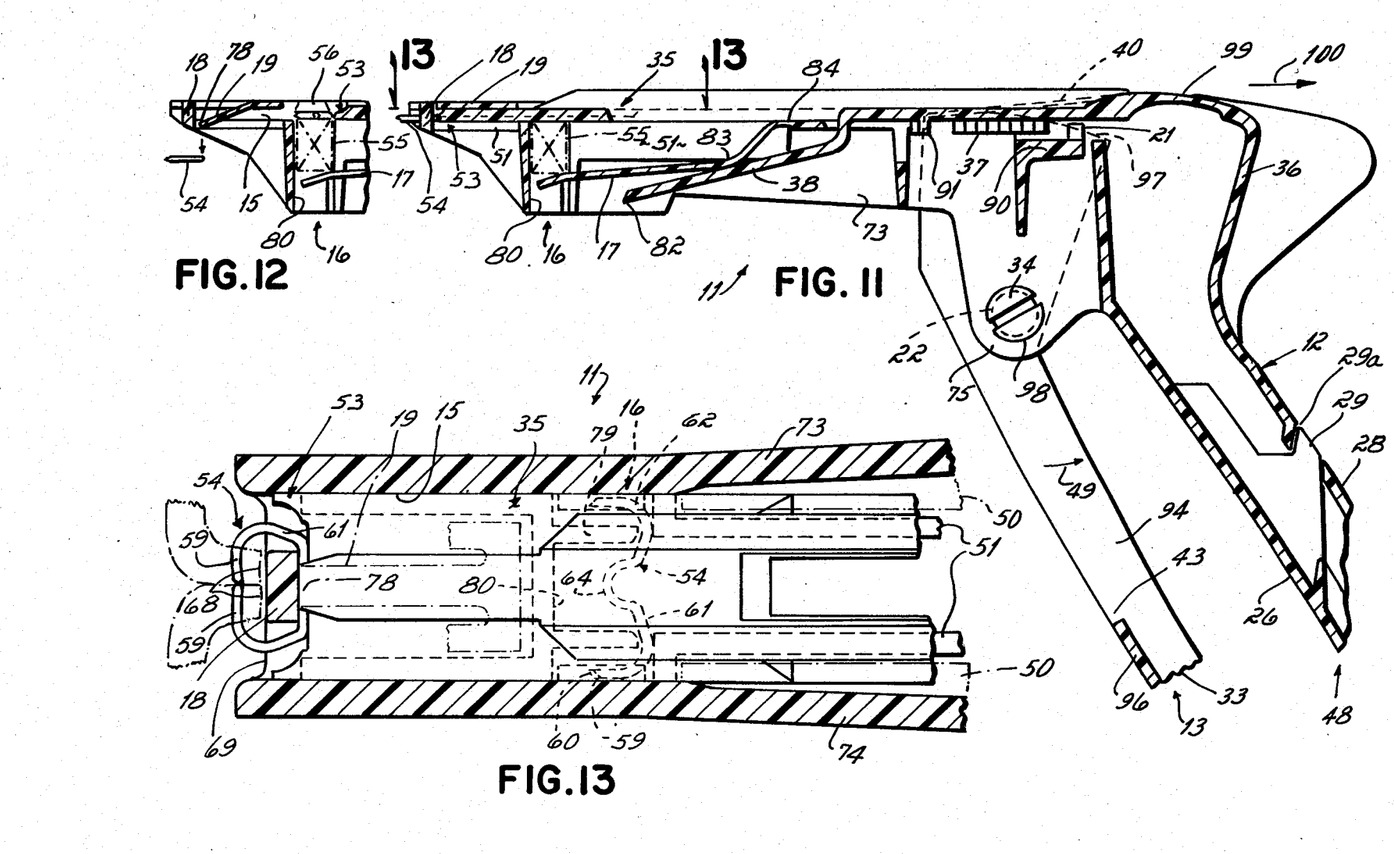
FIG. 11 is a longitudinal vertical section showing the stapler with the trigger fully retracted, the staple having been fully formed.
FIG. 12 is a fragmentary vertical section of the staple supply and anvil portion of the body, showing the staple ejection spring kicking a staple off the anvil.
FIG. 13 is an enlarged, fragmentary horizontal section, somewhat diagrammatic, of the front end portion of the stapler, taken on line 13—13 of FIG. 11, and shows the manner in which stapler is positioned with respect to approximated skin flaps to be stapled together.

Keeping in mind the previously described configuration of the open or unformed staple, the manner in which the staple is closed to hold skin flaps together over a wound can be understood by reference to FIGS. 13, 14A, B, and C. Skin layers 68, 68, on either side of a wound or incision are first proximated, i.e., they are manually held together in facial engagement, as shown in FIG. 13. The tip of the stapler body is notched or recessed, as at 69, so that the overlapped skin flaps can be positioned between the pointed ends 60, 60 of the staple where they can be viewed by the operator.

Outer legs 59, 59, which are straight rather than curved as in the prior art, are provided to impart a better skin gathering ability, and to hold the edges of the wound more tightly together after closure.

The staple is closed by flattening or straightening the rounded center portion 64; there should be essentially no bending at either the outer bends 62 or the inner bends 65. In the closed configuration the staple has a pentagonal "B" shape, shown in FIGS. 13, 14C and 16, defined by the now straightened center section 64, the two straight sections 61, 61, and the two straight legs 59, 59, which are inbent toward the section 64. The tips 60 are brought together and may actually overlap to a small degree, in order to provide for some possible springback after forming. The angle 71 between legs 59, 59 in closed configuration should be about 175°–178° (see FIG. 16). The stapled skin flaps will slide out and apart on the staple legs 59, 59 to the outer bends 62, 62 thereof, so that the two edges of the cut abut for healing. The inbent shape of the staple, with the skin flaps seated on the intermediate sections and the outer bends and the legs inbent toward the center part of the staple, resists rotation about an axis perpendicular to the plane of the staple. The pointed tips remain directly beneath center section 64, which is outside the skin; this facilitates staple removal.

Figure 9:
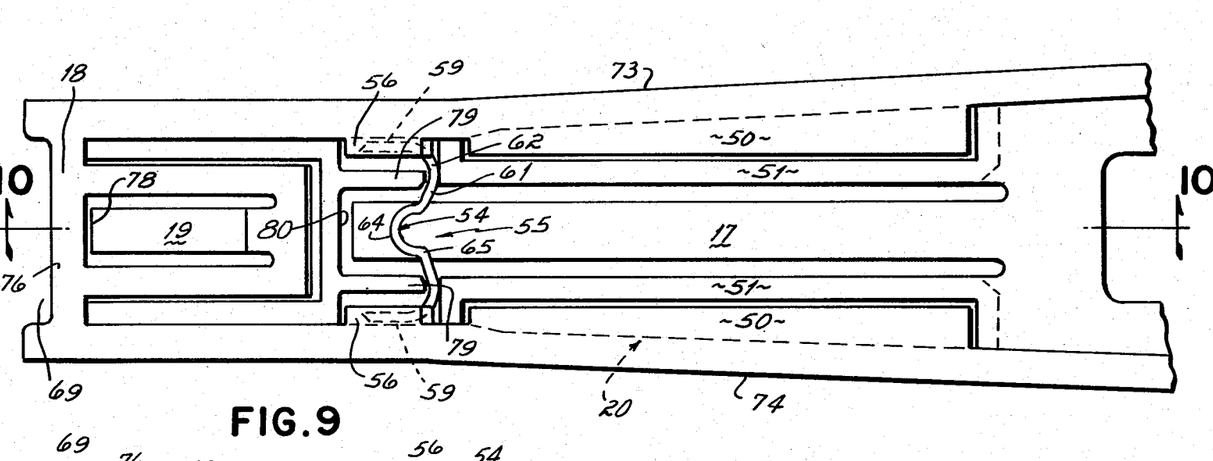
FIG. 9 is an enlarged horizontal section taken on line 9—9 of FIG. 7, with the driver omitted for clarity.
Figure 10:
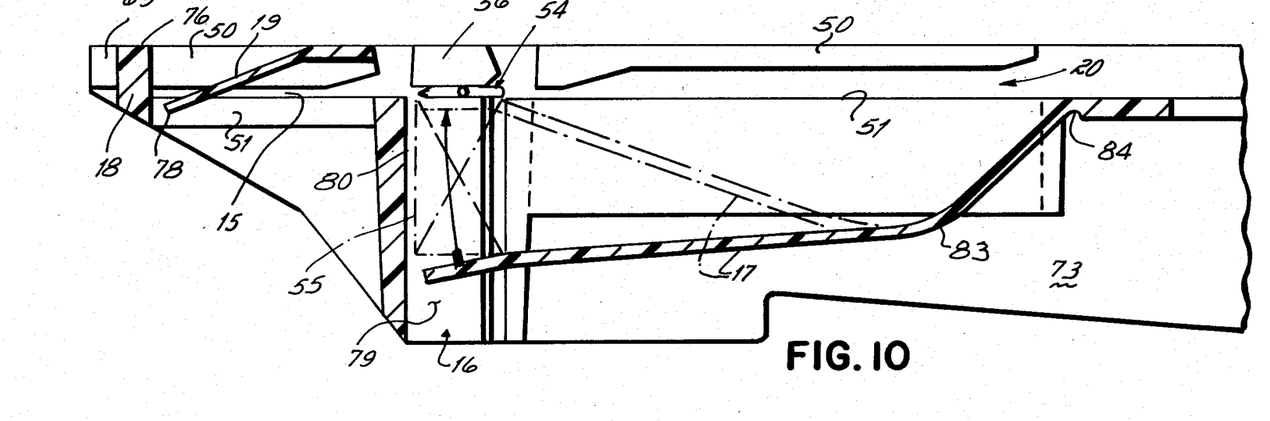
FIG. 10 is a vertical section taken on line 10—10 of FIG. 9.

Given this general description, the parts of the stapler are next discussed in further detail. Stapler body section 11 has two spaced side flanges 73, 74, which are connected to one another at various longitudinal positions by transverse webs or bridges (FIGS. 9 and 10). In the assembled stapler, trigger 33 straddles these body flanges on the outside, and projects approximately perpendicularly to the body. The trigger is pivotally connected to and between opposed openings 22 in ears 75 depending from body flanges 73 and 74.

The anvil or staple forming post 18 depends from web 76 (FIG. 9) into the path of staple movement in staple guide passage 15, defined by and between parallel upper and lower ways 50, 51 (FIG. 10). These ways are formed on the inside surfaces of body flanges 73, 74. Staple ejection spring 19 is presented immediately rearwardly of anvil 18 and is a leaf spring having a tip 78 which exerts a downward bias or spring force on a staple at the anvil, urging the staple downwardly to eject it from anvil 18 (see FIGS. 10, 12, and 14C) when the staple is no longer pressed against the anvil by the driver.

Staples are supplied upwardly from below into staple guide passage 15, from the magazine or supply means 55 (see FIGS. 5 and 10). This magazine 55 has two spaced vertical ribs 79, 79, set in from the respective body flanges, and a center channel or guide 80 between them (FIG. 9). Guide 80 receives and guides the rounded center section 64 of the staples, while the ribs 79, 79 project between the staple legs 59, 59. The stapler may be made as a "low-count" unit, i.e., the supply may be sized to contain only a small number of staples. However, will be apparent that the supply means can be changed to accommodate a greater number of staples.

Figures 7, 8:
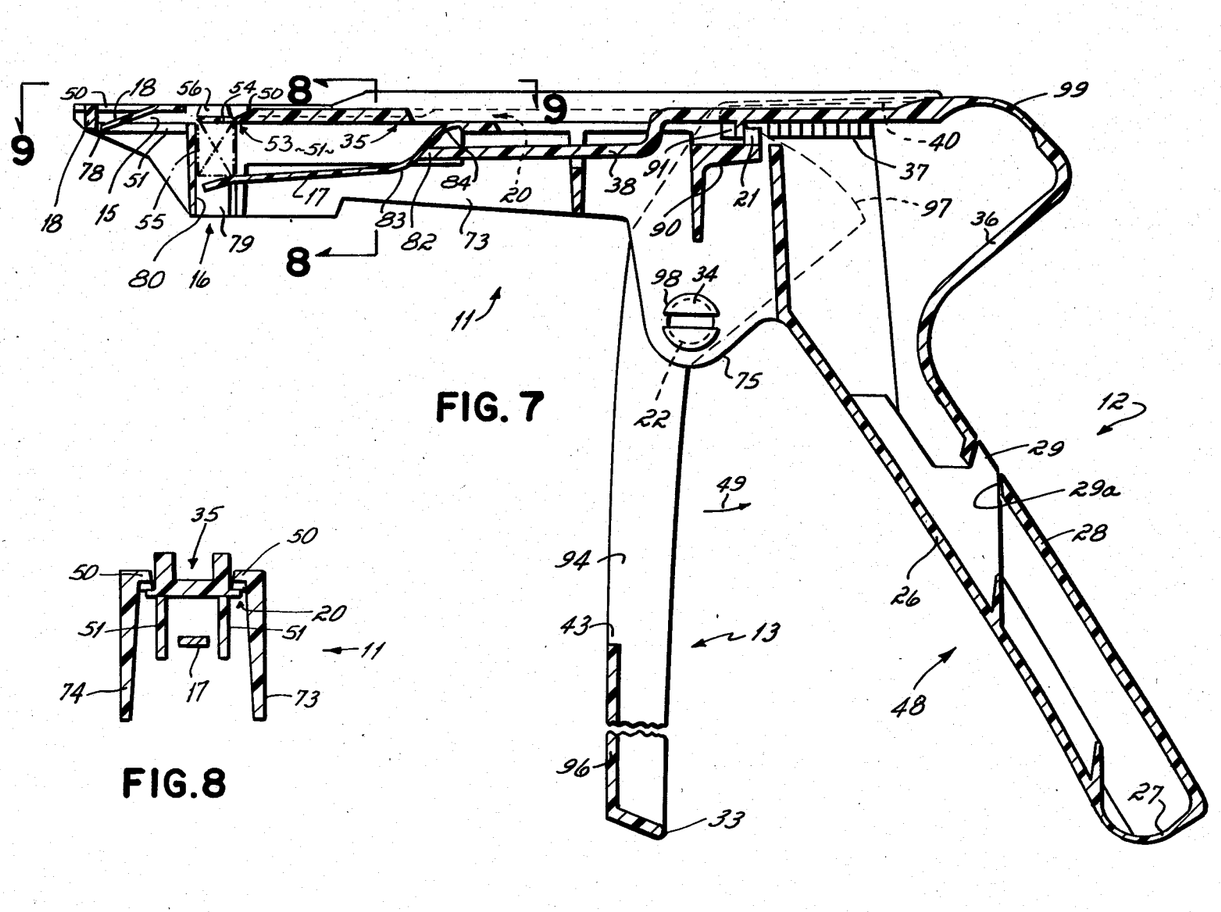
FIG. 7 is a longitudinal vertical section of the stapler after the trigger has been pulled far enough to advance the ratchet to its initial or "cocked" position.
FIG. 8 is an enlarged transverse vertical section taken on line 8—8 of FIG. 7.

The stack of staples 55 is held upwardly by a forwardly projecting cantilever leaf spring 17 which is supported at its rearward end by the two body sides 73, 74. The backup spring 38 projects forwardly from driver 35 (see FIGS. 2 and 3), and in use applies an upward biasing force to feed spring 17, and hence to the staples. When the unit is in the as-shipped condition, as shown in FIG. 5, prior to initial cocking, the supplementary spring 38 is proximate to but does not engage or exert force on feed spring 17. As trigger 33 is pulled, forward motion of the driver brings the tip 82 of the spring into camming and biasing contact with spring 17, as shown in FIG. 7. As the trigger is pulled further, spring 38 applies an increasing force to spring 17, thereby insuring the staples are held upwardly and in contact with the driver. The tip 82 of spring 38 engages spring 17 between a bent knee 83 or crook thereof and the point of attachment 84 to the body, and exerts an upward force on feed spring 17.

Pulling trigger 33 to its fully retracted position shown in FIG. 11 causes the tip 82 of supplementary spring 38 to slide past knee 83, thereby shortening the effective length of the lever acting on spring 17 and increasing the biasing force on stack 55 as the trigger is progressively pulled back. The purpose of the staple feed spring 17 is to apply an upward pressure force on the staples at all times, after the magazine is loaded; the purpose of the backup or supplementary spring 38 is to apply increased force when the driver is "cocked" just prior to first use. This force increases as the driver engages the staple 54, and insures that the staple does not "cock" or get cammed downwardly out of the path of the driver end 53. As will be seen, the spring is not stressed until the gun is cocked immediately prior to first use, which prevents loss of force from plastic creep.

Figure 14B:
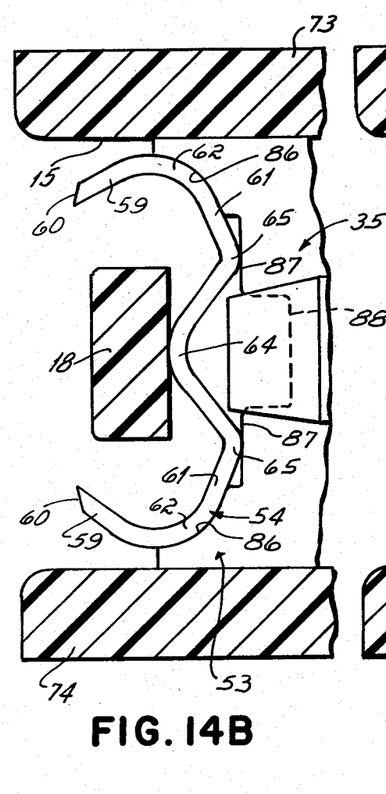
Figure 14C:
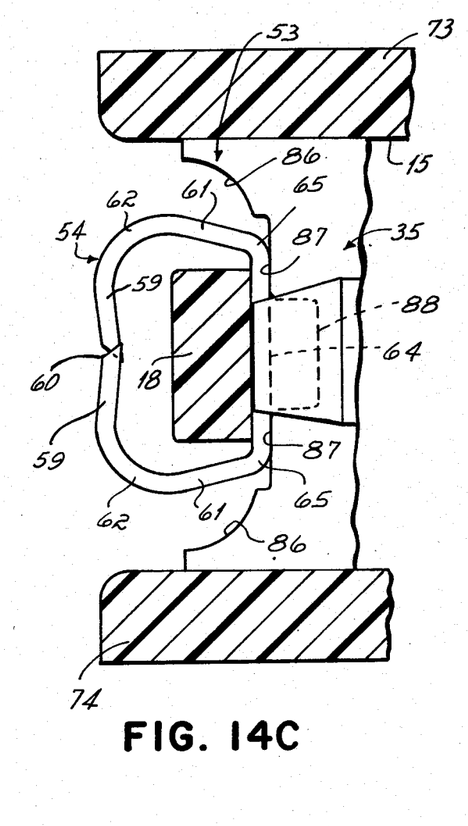

The driver 35 is formed as part of trigger section 13, wherein it projects between the sides of the trigger. The driver is an elongated tongue which is guided and confined in a driver guide channel 20, defined by the guide ways 50, 51 of the body. Driver guide channel 20 is a rearward extension of the staple guide passage 15. The driver has a tip 53 which is specially configured, as best shown in FIG. 14B, to exert a staple bending force which progressively increases as the staple tips 60, 60 are brought together. This is done by reducing the lever arm, and thereby increasing the force applied to the staple by the driver, as the staple is closed. The anvil 18 acts as the fulcrum about which the rounded center 64 of the staple is straightened; force is applied to the staple on each side of the anvil by the driver at points which move inward stepwise, toward the centerline, as the staple is closed. More specifically, driver tip 53 is doubly stepped or recessed, to present longitudinally offset staple centering and forming pockets which engage different parts of the staple as it is progressively formed in clinching. The driver has a pair of first or outer recesses or pockets, shown in FIG. 14A at 86, which engage the outer bends 62, 62 of staple 54. Rearwardly and inwardly of the outer recess sections 86, 86 are inner recesses 87, 87, which engage the staple inner bends 65, 65 (FIG. 14B). A central recess 88 is provided between and rearwardly of the inner recesses 87, 87.

When the driver advances staple 54 to the anvil, the staple is first engaged at its outer bends 62, 62, by the outer recesses 86, 86. These apply force to bend the staple, moving the staple outer bends forward while the staple center 64 is straightened on the anvil. As this occurs, the inner bends 65, 65 come into engagement with driver inner recesses or pockets 87, 87; the lever arm, i.e., the lateral distance between these pockets and anvil 18, is less than that between the anvil and the outer pockets, so that the bending force increases. The tips are brought together smoothly without excessive hand force being required (FIGS. 1B and C). The driver tip engages and lifts staple ejection spring 19 when the staple is being closed; thereafter, when the driver is moved away from the formed staple, spring 19 is released and kicks the staple off anvil 18, as shown in FIG. 12.

It is important that once a staple has been picked up from the magazine and the forming operation has begun, the driver should not be withdrawn or moved back from the staple. If the driver were moved back and thereafter advanced, a second staple could be picked up in the staple guide passage 15 before the first staple was ejected, and jamming could result. In order to prevent the driver from being withdrawn after it has once been moved forward into contact with a given staple, a ratchet mechanism is provided which permits reverse driver movement only after the driver has been advanced to its forwardmost position, corresponding to the ejection of the staple from the anvil. The ratchet mechanism is best seen in FIGS. 5 and 6, and comprises a rack 37 carried by the driver, and a spring-loaded pawl 21 which is presented on a spring member 90 mounted by and between body side flanges 73, 74. The ratchet mechanism also includes a stop 91 which is spaced from the rack on the underside of driver 35. The unit is supplied or shipped with the ratchet in an unstressed condition wherein the pawl is not engaged with either stop 91 or rack 37 (FIG. 5). As trigger 33 is pulled, the driver is advanced into the body, carrying rack 37 in the direction of arrow 92 in FIG. 6. This brings stop 91 into camming engagement with pawl 21. The pawl spring 90 is flexed, allowing pawl 21 to move to the right in FIG. 6, past the stop to the dashed line "Ready" position shown in FIG. 6, and then into engagement with rack 37. The engagement of pawl 21 and rack 37 prevents reverse driver movement. This is shown by the dashed line "Must Complete" position in FIG. 6.

As the driver is advanced, the ratchet rack 37 moves progressively forward past pawl 21, and the pawl seats nearer and nearer the rear of the rack. The pawl spring leg 90 is increasingly deflected, and when the pawl moves beyond the last seat on the rack ("End" in FIGS. 6), the stress of spring 90 snaps the pawl laterally across the end of the rack to the other or flat side 93 of the rack ("Return" position shown in FIG. 6). This permits the rack to be moved rearwardly (to the right in FIG. 6) past the pawl, to disengage and reset in the ready position for the next staple.

Once the pawl has been moved past stop 91 during the first cycle of operation, the stop prevents the driver from returning to the as-shipped position (see FIG. 7).

The driver, as well as rack 37, stop 91, and backup spring 38, are advanced into the body by pulling trigger 33 toward grip 48. Trigger 33 has two spaced sides 94, 95, connected by an end web 96 and defining body aperture 43 between them. These two sides flank but are spaced from driver 35 and backup spring 38. Two tension members, straps or yokes 40,40, connect what in assembled state is the top part 97 of the trigger (above the axle 34 and adjacent retract spring 36) to the driver (FIGS. 1 and 2). In assembled condition, the body extends through aperture 43 between trigger sides 94, 95, so that the trigger straddles the body. As the trigger is pulled, its top part 97 rotates forwardly above the pivots 34, 34; this draws the straps 40, 40 forward, and they draw the driver forwardly with them. The top 97 of the trigger is arcuate or radiused about pivot axles 34, 34 to provide swingable support for the straps.

The trigger straddles and is pivotally connected to apertures in ears, one of which is shown at 75 in FIG. 5, which project below the body sides 73, 74. For this purpose, the pair of stub axles 34, 34 have arrowhead snaps 98, by which they are locked into the pivot openings 22, 22 once the trigger is positioned with respect to the body.

The driver return spring 36 has an S-shape (FIG. 5), and extends forward from rear grip surface 28 to the driver (FIG. 5). This spring has a thin bending portion 99, and is tensioned when the trigger is pulled forward over the body. When the driver is pulled forward by the straps 40, 40, spring 36 exerts a force in the direction of arrow 100 to retract the driver and thereby return the trigger to its normal position.

Having described the invention, what is claimed is:

1. In a stapler having a staple guide passage wherein staples are sequentially engaged by a driver and are formed against an anvil,
   a supply of staples positioned to be fed into said passage for engagement by said driver,
   a feed spring biasing said supply toward said passage, and
   a supplementary spring movable into engagement with said feed spring to supply additional force thereto when said driver is moved to engage a staple from said supply.

2. The stapler of claim 1 wherein said supplementary spring moves with said driver.

3. The stapler of claim 2 wherein said supplementary spring is a cantilever leaf spring projecting from and generally parallel to said driver.

4. The stapler of claim 2 wherein said feed spring is a cantilever leaf spring and said supplementary spring has a tip which is engageable against said feed spring.

5. The stapler of claim 4 wherein said feed spring has a bent knee and said supplementary spring slides over said knee as said driver is advanced.

6. An elongated molding for assembly into a stapler, said molding comprising,
   a body section at one end,
   a trigger section presenting a trigger at an opposite end, and
   a handle section between and interconnecting the body and trigger sections,
   said trigger presenting a body aperture sufficiently wide for the body section to be inserted into it,
   the handle section including a portion which can be flexed to permit the trigger to be brought forwardly over the front end of said body section and the body section inserted into said aperture so that said trigger extends obliquely to the body section, said handle section in use forming a pistol grip by which the stapler is held.

7. The molding of claim 6 formed as a single piece.

8. The molding of claim 6 further including means for connecting said trigger to the body section for pivotal movement toward the grip.

9. The molding of claim 8 wherein said connecting means comprises stub axle means projecting from said trigger, said axle means being receivable in co-acting holes in said body section.

10. The molding of claim 9 further wherein said stub axle means includes snap-in means for preventing the axle means from being withdrawn from said holes.

11. The molding of claim 10 wherein said body aperture is presented between said sides.

12. The molding of claim 6 wherein said trigger includes two sides connected by a transverse web, said sides and web forming said trigger.

13. The molding of claim 6 further including a staple driver,
    said body section including a driver guide channel into which said driver can be inserted as the body section is being inserted into said body aperture,
    said channel positioning the driver for longitudinal movement in the body section.

14. The molding of claim 13 wherein said driver is formed between sides of said trigger.

15. The molding of claim 14 further wherein the trigger section includes driver advancing means connecting said trigger to said driver for advancing said driver in said channel when said trigger is pulled.

16. The molding of claim 13 further wherein said trigger includes pivot means connectable to the body so that the trigger can be pivoted toward the grip,
    said trigger having a top part which in use is above said pivot means and which moves forwardly as the trigger is pulled toward the grip, and
    driver advancing means comprising at least one strap connected between said top part of the trigger, and said driver.

17. The molding of claim 13 including a driver retract spring comprising a spring portion between the grip and the driver,
    said spring portion being stressed in use as said trigger is pulled, so that it exerts a retracting force on said driver.

18. The molding of claim 17 wherein said spring portion extends between said grip and what in use is the rear end of said driver.

19. The molding of claim 18 wherein said spring portion has a S-shape.

20. The molding of claim 6 wherein said handle section includes a front part and a rear part and latch means for securing said parts together.

21. The molding of claim 6 wherein the body section includes a staple supply and a staple feed spring for urging said supply toward a staple guide passage in said body section.

22. The molding of claim 21 further including an anvil on said body section at a front end of said guide passage,
    said anvil having a depth approximating the thickness of a staple.

23. The molding of claim 22 further including a staple ejection spring in said body section for ejecting a staple from said anvil after closing.

24. The molding of claim 23 wherein said staple ejection spring is a leaf spring which projects from said body section into said staple guide passage.

25. The molding of claim 21 wherein said feed spring is a leaf spring projecting forwardly in said body section.

26. The molding of claim 21 further including a staple driver and a backup spring which extends from said driver and which in use is brought into assisting relation with said feed spring as said driver is moved to engage a staple in said guide passage.

27. The molding of claim 26 wherein said feed spring is formed with a bent knee, and said backup spring is shaped to slide over said knee in use.

28. The molding of claim 21 wherein said staple supply is located below said guide passage to feed staples into it at substantially a right angle thereto.

29. The molding of claim 6 further including ratchet means for preventing said driver from being withdrawn from a staple once the driver has engaged that staple.

30. The molding of claim 29 further wherein said trigger section includes a driver moved by the trigger in the assembled stapler, and said ratchet means includes a rack and a pawl,
said rack being mounted to and moving with said driver.

31. The molding of claim 30 wherein the pawl is mounted from said body section by a spring,
the rack being disengaged from the pawl until said stapler is used for the first time.

32. The molding of claim 30 further including a stop between said rack and said pawl so positioned that in use it limits movement of said rack away from said pawl.

33. An elongated molding for assembly into a stapler, said molding comprising,
a body section at one end,
a trigger section presenting a trigger at an opposite end, and
a handle section between and interconnecting the body and trigger section,
a handle section adapted to form a pistol grip by bending back on itself, and
integral means for pivotally mounting the trigger angularly to the body section, in front of the grip.

34. The molding of claim 33 wherein the handle section includes a front part, a rear part, and a flexible butt part connecting the front and rear parts, whereby said rear part can be swung generally parallel to the front part to form said pistol grip.

35. The molding of claim 34 wherein said trigger section extends from the rear part of said handle section.

36. The molding of claim 35 wherein a driver is formed in said trigger section, between spaced sides of said trigger.

37. The molding of claim 36 wherein said trigger section includes straps which connect said trigger to the rear part of said handle section.

38. The molding of claim 37 further including a retract spring between the trigger and the grip, and wherein said driver is aligned with and extends from said retract spring.

39. The molding of claim 34 wherein said retract spring forms an S-shape upon assembly of said molding.

40. A stapler comprising,
a body, a trigger pivotally connected to said body, and a pistol grip,
said trigger being pivoted to said body and swingable rearwardly about its pivot, toward said grip,
a driver slidable in said body in a driver guide channel therein,
said trigger including a top part which rotates forwardly when said trigger is pivoted toward said grip, and
strap means connected between said top part of said trigger and said driver, to pull the driver in said guide channel as said trigger is pulled.

41. The stapler of claim 40 further including ratchet means for preventing said driver from being withdrawn from a staple once the driver has engaged the staple,
said ratchet means including a rack and a pawl, said rack being mounted to and moving with said driver, said pawl being mounted to said body.

42. The stapler of claim 41 wherein said pawl is mounted on a spring arm from said body.

43. The stapler of claim 42 further including a stop on said driver between said rack and said pawl which limits movement of said rack away from said pawl.

44. The stapler of claim 40 further wherein said body extends through a body aperture in said trigger.

45. The stapler of claim 40 wherein said trigger includes two sides connected by a transverse web, said body aperture is presented between said sides, and said body extends through said aperture in said trigger.

46. The stapler of claim 45 wherein said trigger is connected to said body by stub axle means projecting from said trigger, said axle means being received in co-acting holes in said body.

47. The stapler of claim 46 further wherein said stub axle means includes snap acting means for preventing the axle means from being withdrawn from said holes.

48. The stapler of claim 40 wherein said driver is formed integrally with said trigger and is connected to it by said strap means.

49. The stapler of claim 40 including an S-shaped driver retract spring connected between said driver and said grip.

50. The stapler of claim 49 wherein said driver retract spring is a strip of flexible plastic, and is integral with both said driver and said grip.

51. The stapler of claim 40 further including a staple supply and a staple feed spring for urging said supply toward a staple guide passage, said feed spring being a leaf spring, and
a backup spring extending from said driver and which is brought into assisting relation with said feed spring as said driver is moved to engage a staple in said guide passage.

52. The stapler of claim 51 wherein said feed spring is formed with a bent knee, and said backup spring engages said feed spring between said knee and said driver.

53. The stapler of claim 52 wherein said backup spring is unstressed until said trigger is pulled to engage a staple.

54. The stapler of claim 53 wherein said backup spring exerts increasing force on said feed spring as a staple is being formed.

* * * * *